United States Patent [19]
Packer et al.

[11] Patent Number: 5,184,720
[45] Date of Patent: Feb. 9, 1993

[54] SHARPS COLLECTOR

[75] Inventors: Gilbert Packer, Carlsbad; Rex O. Bare, Lake Forest; Richard Shillington, Leucadia, all of Calif.

[73] Assignee: Med-Safe Systems, Inc., Carlsbad, Calif.

[21] Appl. No.: 789,739

[22] Filed: Nov. 8, 1991

[51] Int. Cl.⁵ .................. B65D 83/02; B65D 83/10
[52] U.S. Cl. .................... 206/366; 206/499; 206/1.5; 206/459.5; 220/335; 220/336; 220/339; 220/315; 220/380; 220/DIG. 12; 220/DIG. 14; 220/4.01; 220/763
[58] Field of Search .......... 206/364, 365, 366, 499, 206/1.5, 459; 220/335, 336, 339, 315, 380, 94 A, DIG. 12, DIG. 14, 4.01

[56] References Cited

U.S. PATENT DOCUMENTS

| | | | |
|---|---|---|---|
| 3,226,007 | 12/1965 | Thies et al. | 206/366 X |
| 4,488,643 | 12/1984 | Pepper | 206/366 |
| 4,715,498 | 12/1987 | Hanifl | 206/366 |
| 4,828,107 | 5/1989 | Spencer | 206/366 |
| 4,842,138 | 6/1989 | Sandel et al. | 206/366 X |
| 4,869,366 | 9/1989 | Bruno | 206/366 |
| 4,874,103 | 10/1989 | Quisenberry et al. | 206/366 X |
| 4,890,733 | 1/1990 | Anderson | 206/366 X |
| 4,927,076 | 5/1990 | Simpson | 206/366 X |
| 4,930,631 | 6/1990 | Bruno | 206/366 X |
| 5,014,874 | 5/1991 | Kitsos et al. | 206/366 X |
| 5,031,767 | 7/1991 | Bruno | 206/366 X |
| 5,046,614 | 9/1991 | Torres et al. | 206/366 |
| 5,080,251 | 1/1992 | Noack | 206/366 |

Primary Examiner—William I. Price
Attorney, Agent, or Firm—Lyon & Lyon

[57] ABSTRACT

A sharps collector comprising a container for holding, storing, and disposing syringes. The sharps collector includes a disposable receptacle and a decorative cover. The receptacle preferably has two elongated apertures and chutes associated with each aperture. The chutes are designed to guide syringes into the receptacle once the syringes pass through an aperture. The chutes also obstruct syringes which are already contained in the receptacle from protruding or re-emerging out of the receptacle. The decorative cover is reusable and fits over and attaches to the receptacle. When the cover is attached to the receptacle, it conceals the apertures and chutes of the receptacle. The cover includes an elongated aperture through which a shuttle is accessed. The shuttle directs syringes to the concealed apertures and chutes of the receptacle. The syringes to be disposed are placed in the shuttle and the shuttle is manually shifted such that a syringe is pushed towards an aperture and chute. The syringe then falls through the aperture, is guided by the chute, and ultimately falls into the receptacle and is contained within the receptacle. The cover can be detached from a receptacle when that receptacle is ready to be discarded.

30 Claims, 16 Drawing Sheets

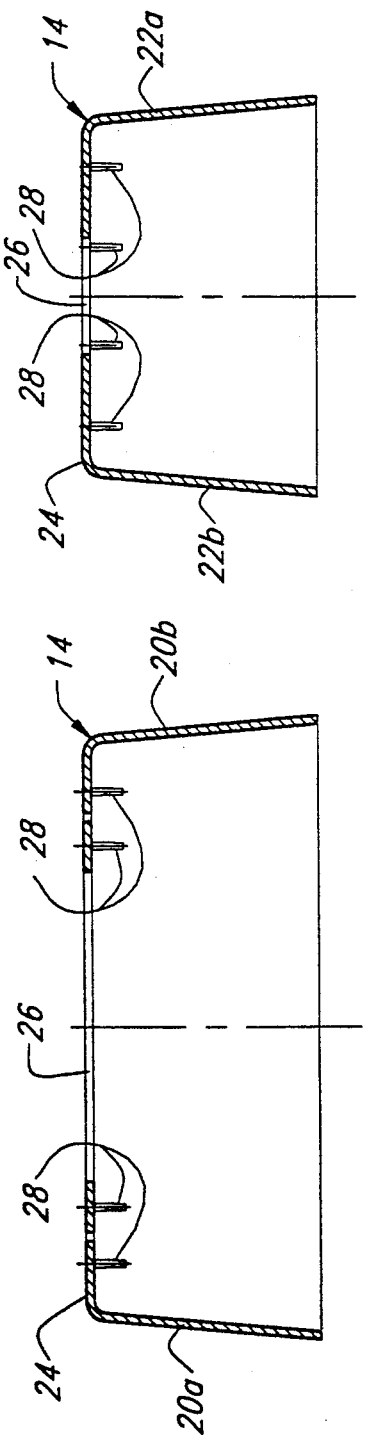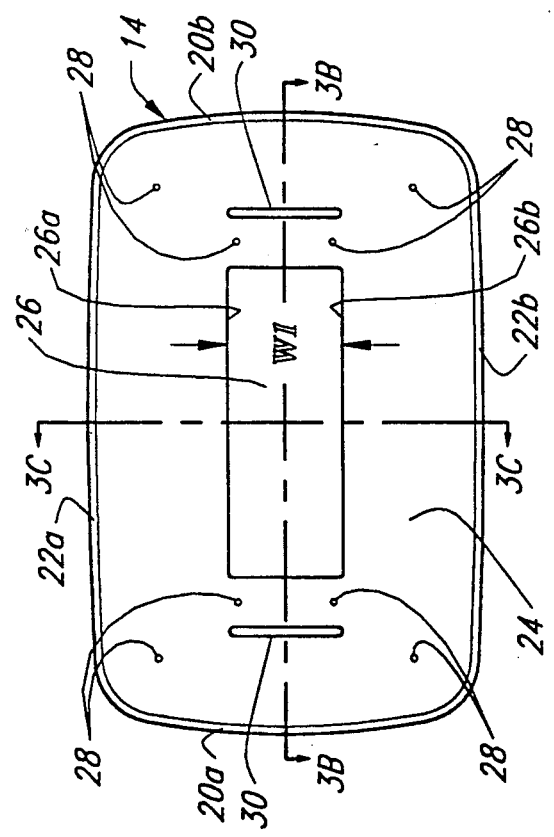

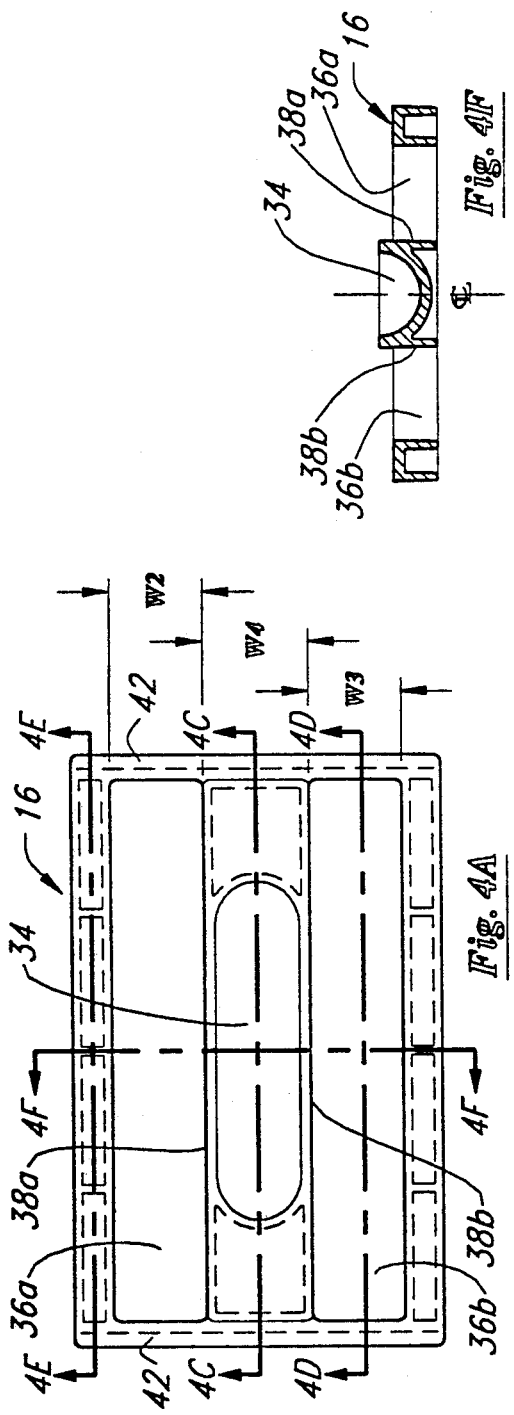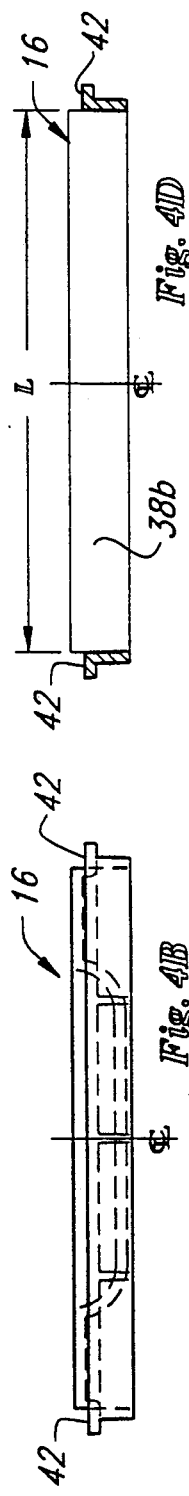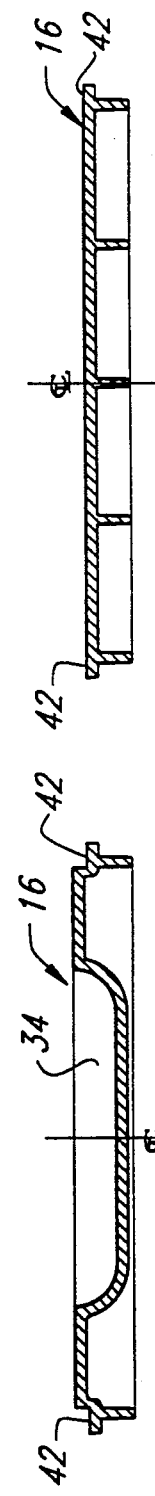

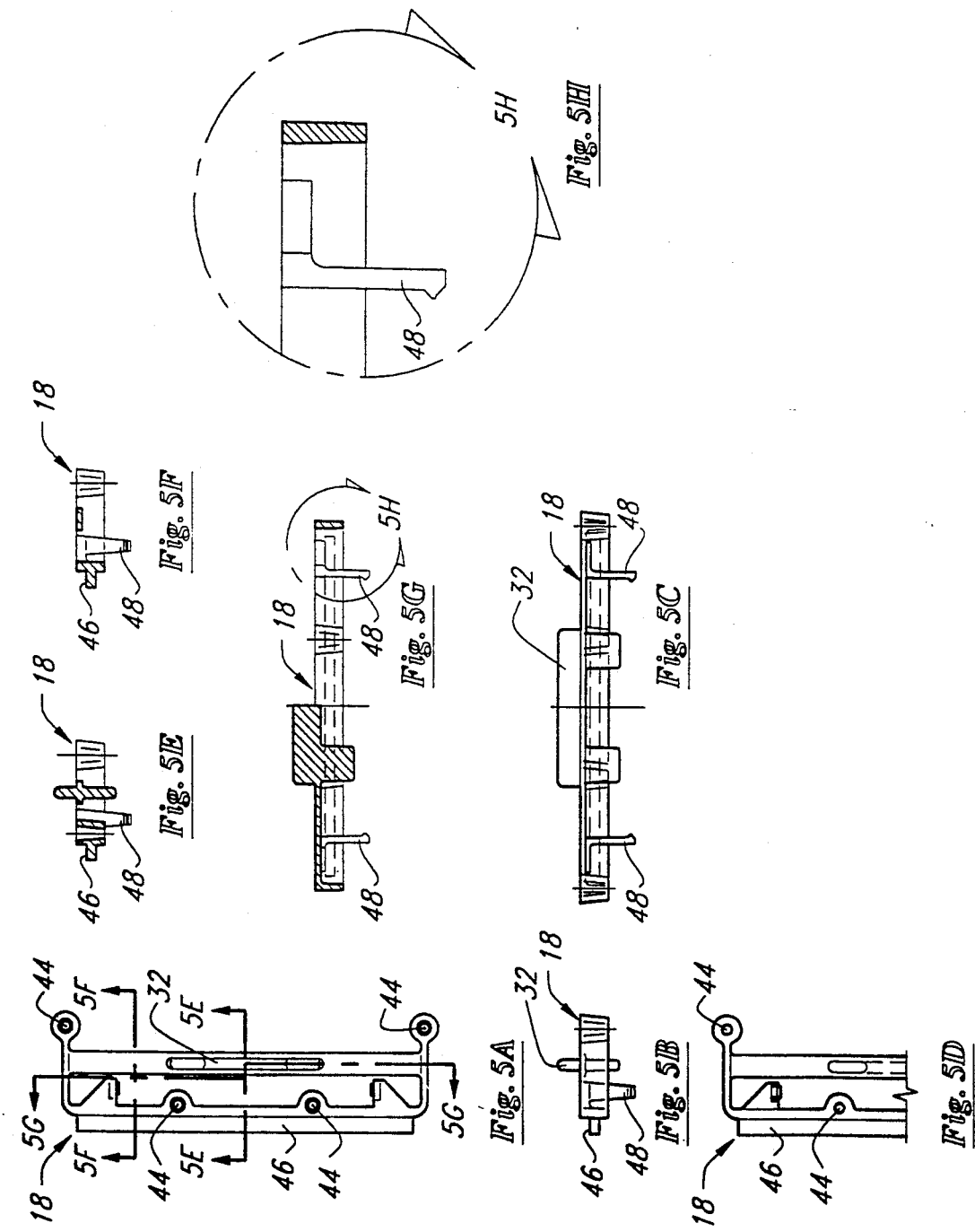

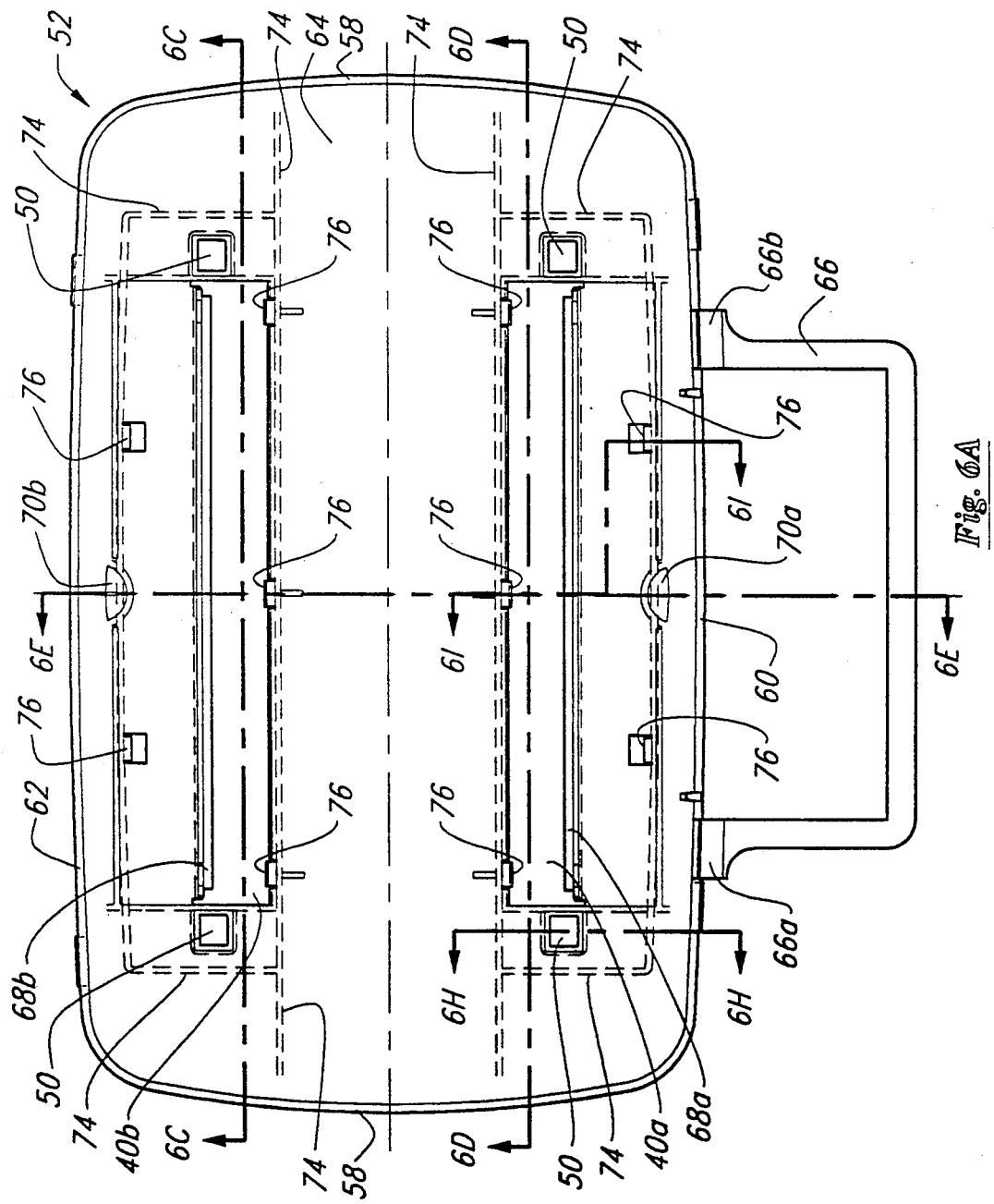

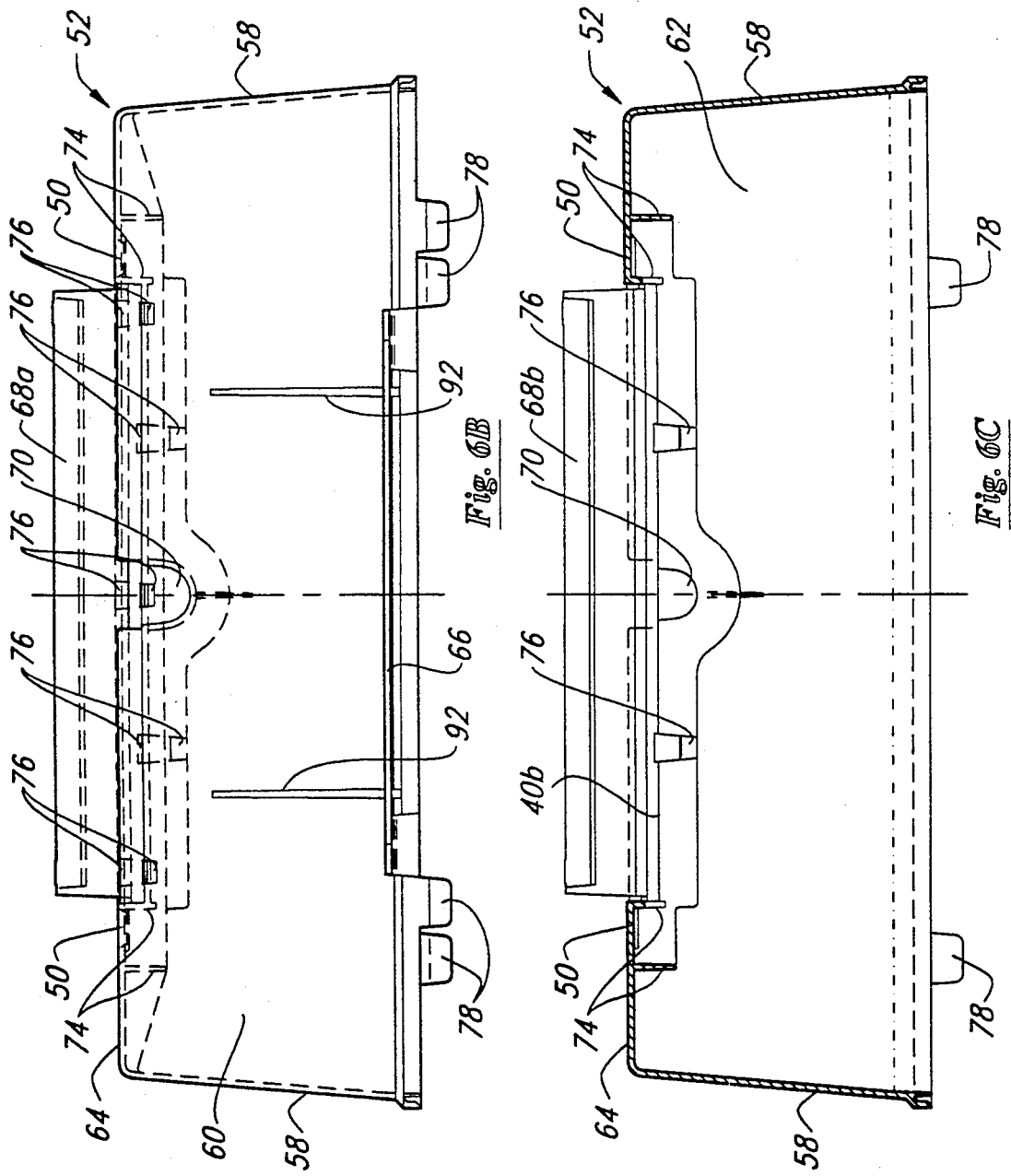

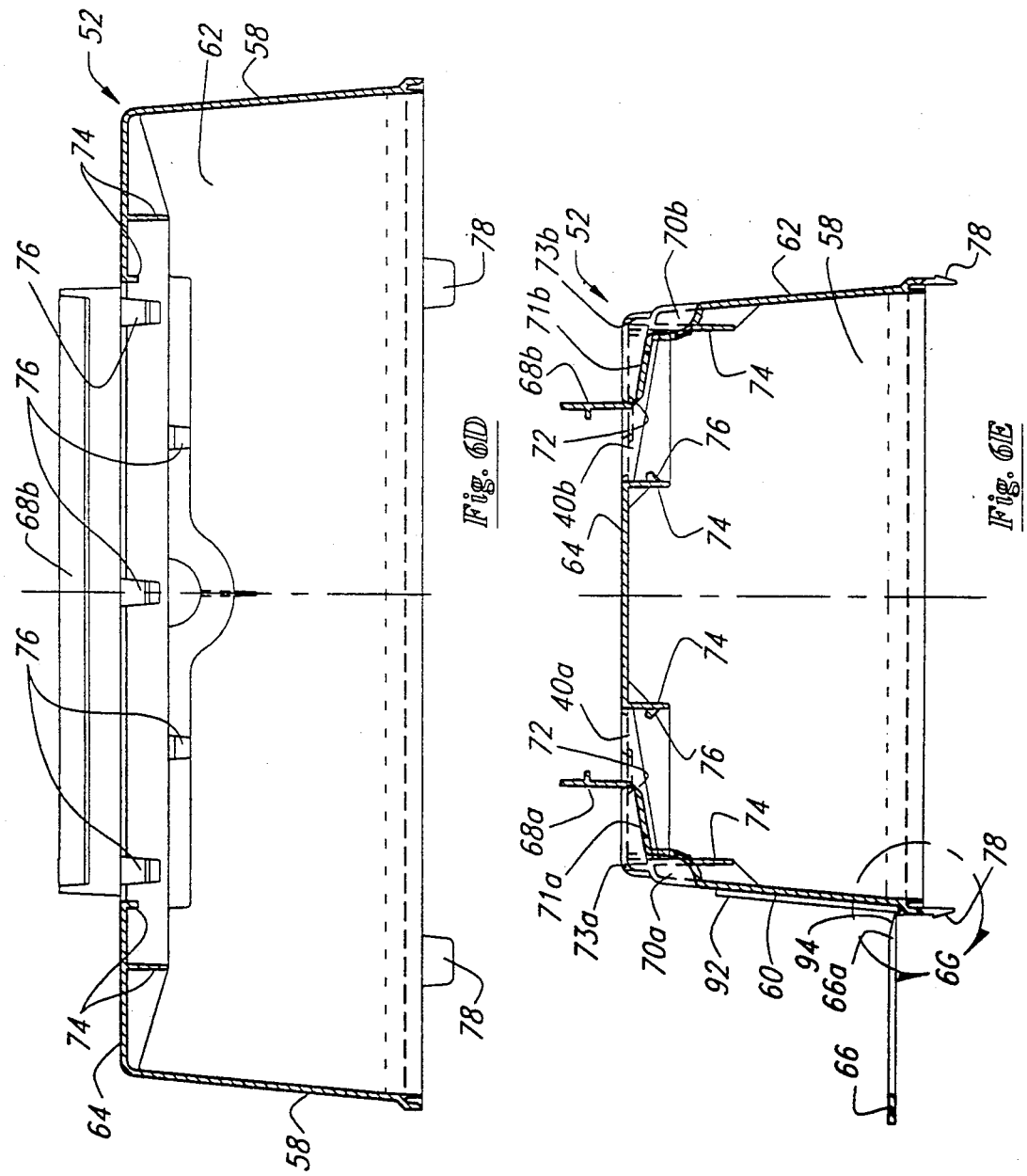

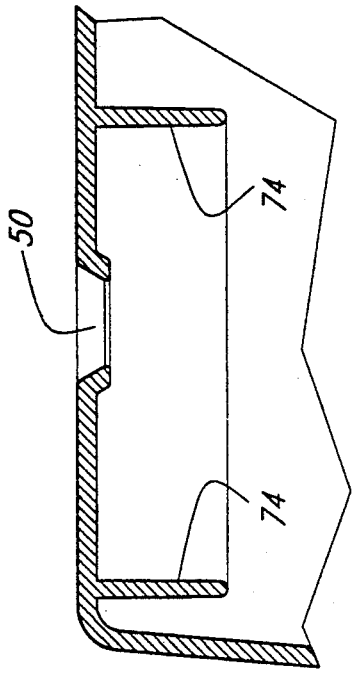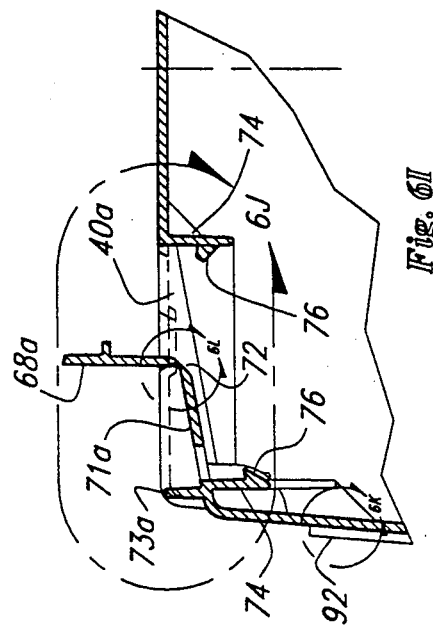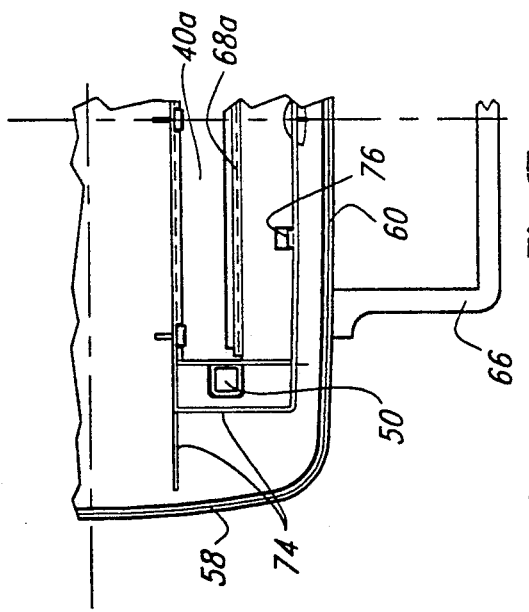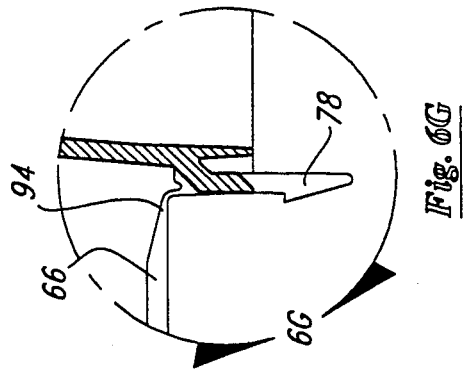

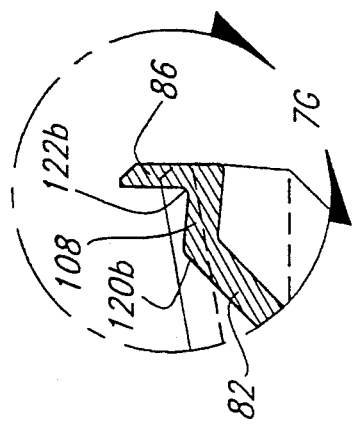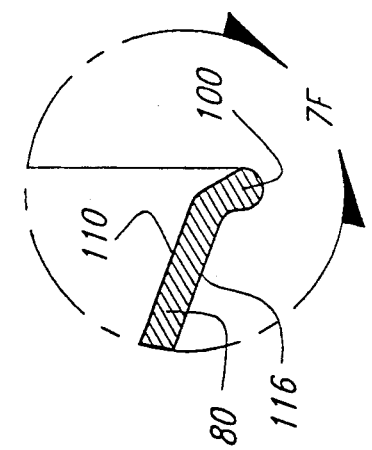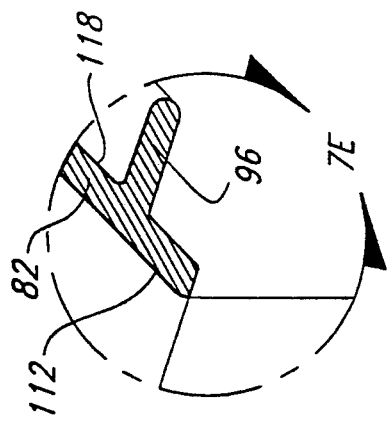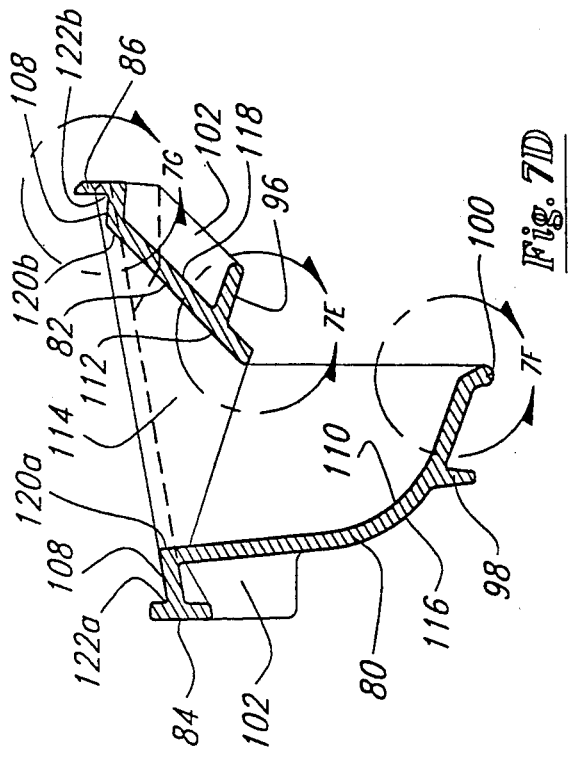

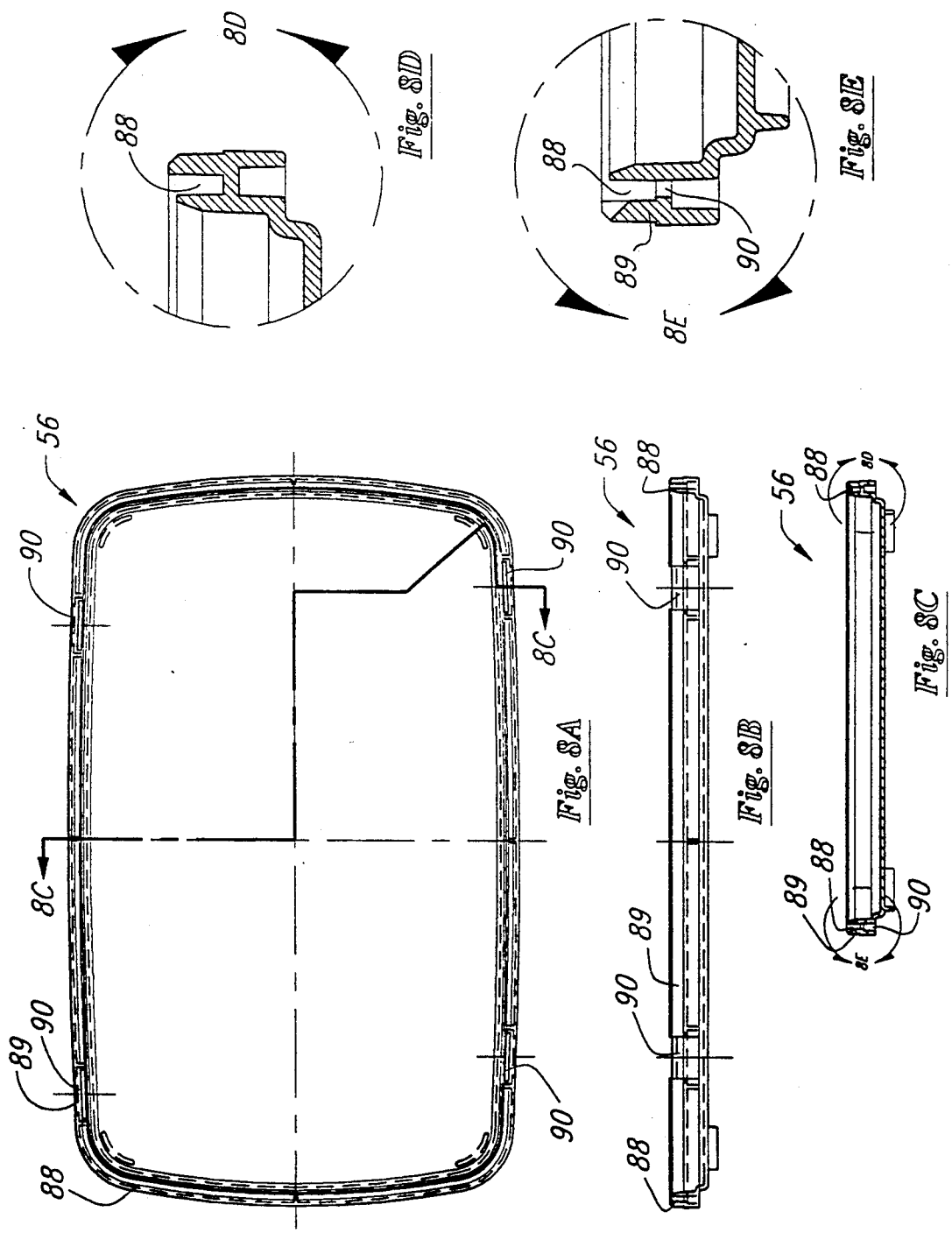

SHARPS COLLECTOR

INTRODUCTION

The present invention relates to collector devices, and more particularly to a "sharps" collector for devices such as syringes.

BACKGROUND OF THE INVENTION

The term "sharps" applies to any sharp device used in medical applications, such as hypodermic needles, lances, and the like. The dangers of disposing of these devices after use have become more prevalent with expanding diseases such as AIDS and hepatitis. Before disposal, the used devices must be contained such that exposure to others is minimized. These disposal problems are present in hospitals and doctor's offices, and are also present in home settings. Diabetics, for example, and others must dispose of numerous used needles and syringes. There are presently over two million diabetics in the United States, each of whom use an average of one and one-half syringes per day.

In addition to the problem of providing a receptacle for receiving used syringes, the container itself must be disposable, hold a reasonable number of syringes, insure that the syringes are stacked or packed in some suitable way, be safe to use without a deposited syringe sticking out or reemerging from the receptacle, be secure so that a child or animal cannot reach in and injure themselves on the discarded syringes contained therein, be closeable for disposal, and be puncture resistant, leak resistant, break resistant, as well as be tamper resistant after being closed and tamper evident if opened. The use of nontoxic materials and incineratable materials is important because some receptacles are incinerated and/or disposed of at disposal sites. Also, for use in doctor's offices the receptacles may need to be autoclavable.

SUMMARY OF THE INVENTION

The present invention is intended to meet the foregoing requirements while solving many of the problems associated with the storage and disposal of used syringes. The present invention relates to a sharps collector including a disposable receptacle for receiving syringes in particular, and other sharps in general. A preferred and exemplary embodiment of the invention as shown and described herein is particularly designed for insulin syringes (0.3, 0.5 and 1.0 ml.). The collector preferably also includes a reusable decorative cover. The receptacle and cover can be packaged together in a box with new syringes for shipment and sale.

The receptacle is a box-like structure and includes a pair of apertures which act as access ports and have specially designed chutes for permitting different sized syringes to fall into the receptacle and be prevented from reemerging. The receptacle also has a pair of aperture covers which provide locking doors and may be flipped over the respective apertures and chutes, and snapped securely closed to make the receptacle tamper resistant once it is full and ready for final disposal.

The chute design allows different sizes of syringes, with or without attached needles, to reliably fall into the receptacle in an organized and reasonable manner. The design shown and described herein is for 0.3, 0.5 and 1.0 ml. insulin syringes. The cover has a shuttle for directing syringes to the apertures and chutes. The chute and shuttle designs cause the syringes to align with the longitudinal axis of the chute and to fall evenly into the receptacle. Thus, the syringes can fall into the receptacle in a manner which ensures efficient use of space. This "stacking" scheme enables the syringes to be inserted in a horizontal orientation and fall horizontally ("horizontal drop") into the receptacle and ensures that the receptacle will hold a reasonable number of syringes while enabling a relatively low profile container to be provided. In addition, the chute design prevents any syringes from protruding out of the receptacle and from being easily reached or removed.

The reusable cover is provided to fit over the disposable receptacle. However, the disposable receptacle can be used with or without the cover. The cover also has the shuttle, termed a double shuttle, which serves top-push the used syringes toward a particular aperture and chute, and cause each syringe to descend into the receptacle. The cover and shuttle allow the syringes to be alternately discarded into the receptacle through one, and then the other, of the chutes. Using the chutes alternately helps ensure an even distribution and nesting of the syringes within the receptacle and, thus, the efficient use of space within the receptacle. Although two apertures and chutes are used in the present preferred embodiment to help distribute the syringes and hold down the container size and center of gravity through the use of "horizontal drop," a single aperture and chute can be used.

The cove preferably is designed such that it can be snapped onto, and locked with, the underlying receptacle but be quickly and simply unlocked for reuse when the disposable receptacle is discarded. This locking arrangement renders the collector child resistant and tamper resistant. The cover and shuttle design provides the further benefit of completely concealing from view the aperture and chute features of the disposable receptacle. The chute design, along with the cover and shuttle designs, render beyond reach the syringes which are enclosed in the receptacle.

BRIEF DESCRIPTION OF THE DRAWINGS

FIG. 3A is a bottom view of a decorative cover of the collector.

FIG. 3B is a cross-sectional view of the cover taken along line 3B—3B in FIG. 3A.

FIG. 3C is a cross-sectional view of the cover taken along line 3C—3C in FIG. 3A.

FIG. 4A is a top view of a double shuttle for use with the cover of the present invention.

FIG. 4B is a side view of the double shuttle.

FIG. 4C is a cross-sectional view of the double shuttle taken along line 4C—4C in FIG. 4A.

FIG. 4D is a cross-sectional view of the double shuttle taken along line 4D—4D in FIG. 4A.

FIG. 4E is a cross-sectional view of the double shuttle taken along line 4E—4E in FIG. 4A.

FIG. 4F is a cross-sectional view of the double shuttle taken along line 4F—4F in FIG. 4A.

FIG. 5A is a top view of one of a pair of guides for the double shuttle of the present invention.

FIG. 5B is a front view of the guide.

FIG. 5C is a side view of the guide.

FIG. 5D is a fragmentary view of the bottom side of the guide.

FIG. 5E is a cross-sectional view of the guide taken along line 5E—5E in FIG. 5A.

FIG. 5F is a cross-sectional view of the guide taken along line 5F—5F in FIG. 5A.

FIG. 5G is a cross-sectional view of the guide taken along line 5G—5G in FIG. 5A.

FIG. 5H is a detailed enlargement of an attachment hook of the guide taken from circle 5H in FIG. 5G.

FIG. 6A is a top view of a top section of a disposable receptacle of the present invention.

FIG. 6B is a front view of the top section.

FIG. 6C is a cross-sectional view of the top section taken along line 6C—6C in FIG. 6A.

FIG. 6D is a cross-sectional view of the top section taken along line 6D—6D in FIG. 6A.

FIG. 6E is a cross-sectional view of the top section with aperture covers in an open position taken along line 6E—6E in FIG. 6A.

FIG. 6F is an enlarged partial bottom view of the top section.

FIG. 6G is a detailed enlargement of a tab part of an attachment mechanism of the disposable receptacle taken from circle 6G in FIG. 6E.

FIG. 6H is an enlarged cross-sectional view of an attachment slot of the disposable receptacle taken along line 6H—6H in FIG. 6A.

FIG. 6I is an enlarged cross-sectional view of an aperture and aperture cover of the disposable receptacle with the aperture cover in an open position taken along line 6I—6I in FIG. 6A.

FIG. 7D is a cross-sectional view of the chute taken along line 7D—7D of FIG. 7A.

FIG. 7E is an enlarged view of a stiffener rib of the chute taken from circle 7E in FIG. 7D.

FIG. 7F is an enlarged view of a stiffener rib of the chute taken from circle 7F in FIG. 7D.

FIG. 7G is an enlarged view of an attachment ledge of the chute taken from circle 7G in FIG. 7D.

FIG. 8A is a top view of a bottom closure of the disposable receptacle of the present invention.

FIG. 8B is a side or elevational view of the bottom closure.

FIG. 8C is a cross-sectional view of the bottom closure taken along line 8C—8C in FIG. 8A.

FIG. 8D is an enlarged cross-sectional view of a portion of the bottom closure taken from circle 8D in FIG. 8C.

FIG. 8E is an enlarged cross-sectional view of a tab receiving slot part of an attachment mechanism of the bottom closure taken from circle 8E in FIG. 8C.

DESCRIPTION OF THE PREFERRED EMBODIMENT

Figure 1:
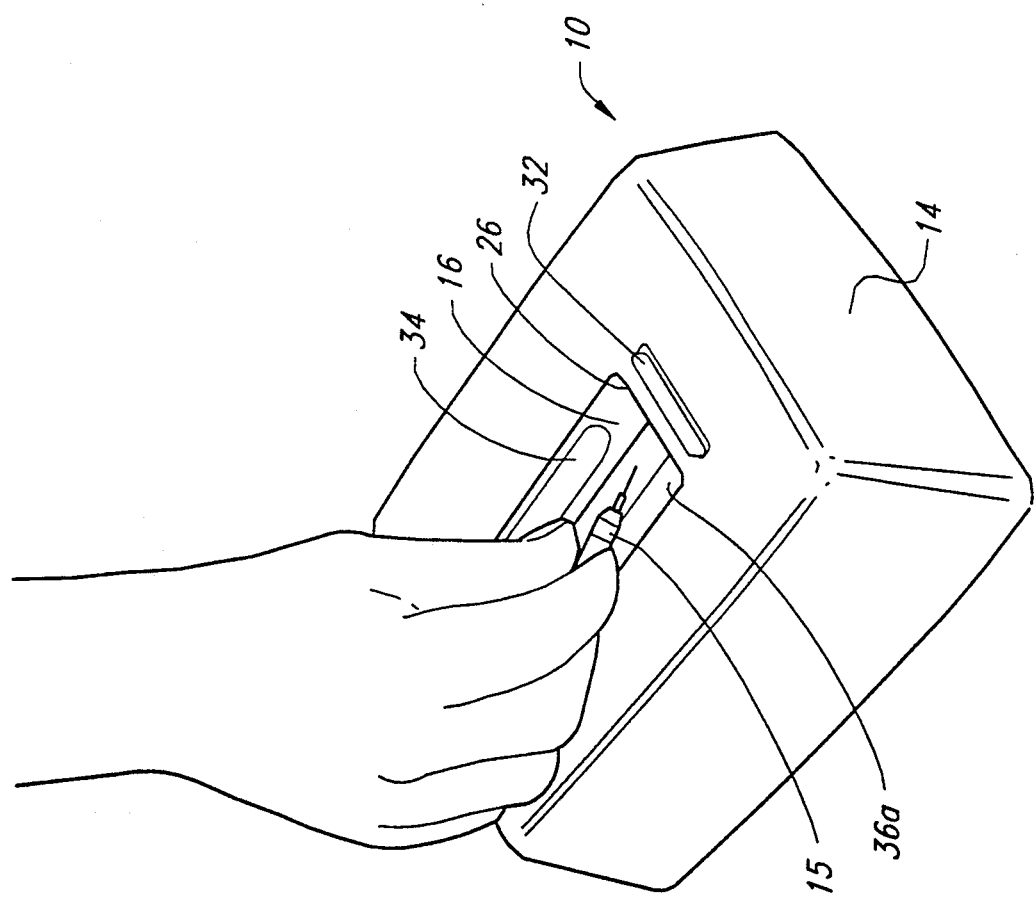
FIG. 1 is a perspective view of a complete sharps collector of the present invention as it is used.
Figure 2B:
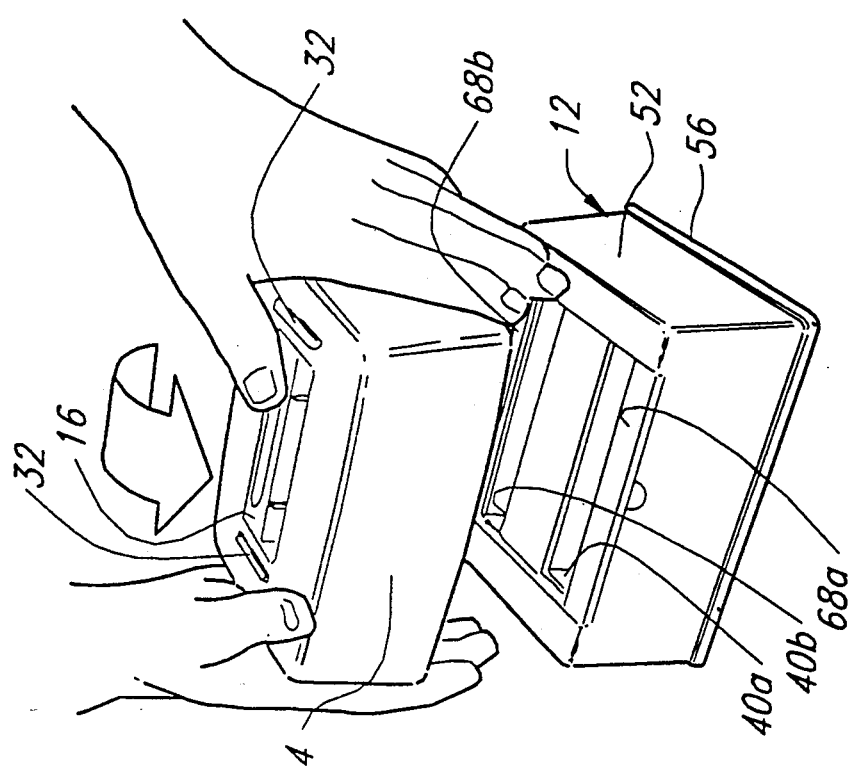
FIG. 2B is a perspective view of a disposable receptacle of FIG. 1 as a decorative cover of FIG. 1 is being attached.

Turning now to the drawings, and first to FIGS. 1 and 2, FIG. 1 shows a perspective view of the preferred embodiment of the present invention in the form of a sharps collector 10 having a reusable decorative cover 14. As shown in FIG. 2B, the sharps collector 10 includes an inner disposable receptacle 12 which can be covered by the outer reusable cover 14. This sharps collector 10, for receiving insulin syringes as noted earlier, is about the size of a facial tissue box.

Figure 2A:
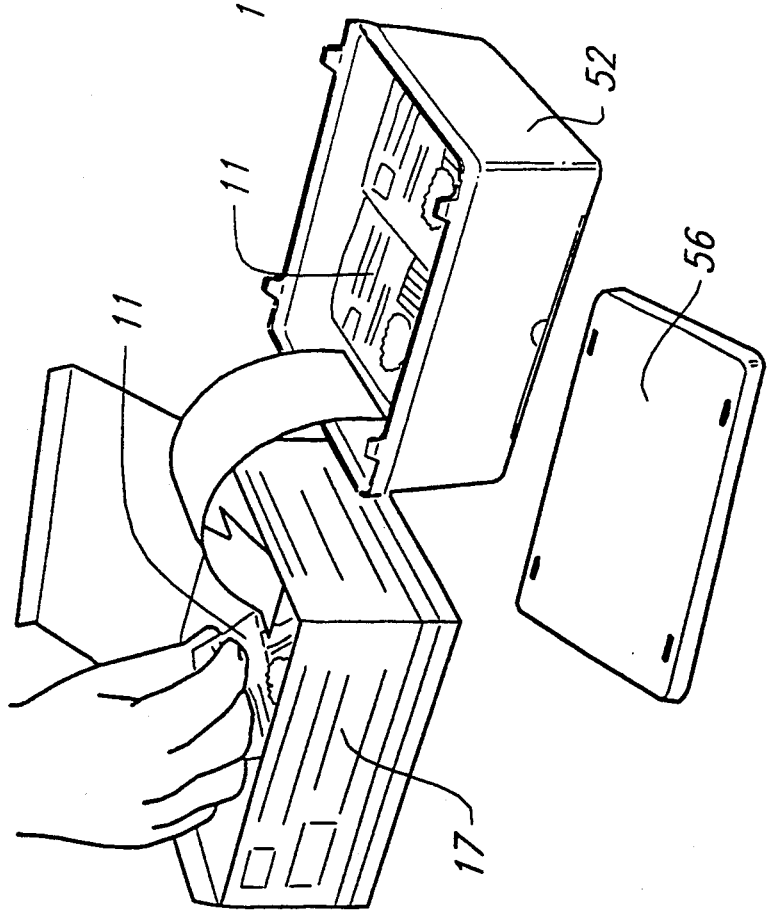
FIG. 2A is a perspective view of the disposable receptacle of FIG. 2B as packaged syringes are removed therefrom in preparation for use.

The receptacle 12 comprising a top section 52 and bottom closure 56, along with the cover 14 and packages of syringes 11 (e.g., 100) can be nested together and shipped and sold in a suitable box 17 as seen in FIG. 2A. These are removed from the box 17 and the collector 10 assembled. The collector 10 is assembled by snapping the bottom closure 56 and top section 52 together to form the receptacle 12. This is usually accomplished by laying the top section 52 upside down on a table and snapping the bottom closure 56 firmly on the section 52. Then, the cover 14 is snapped onto the disposable receptacle 12 as shown in FIG. 2B and locked together in a manner which will be further explained later.

The sharps collector 10 is used by placing a syringe 15 into a slot 36a which is exposed on the top of the collector 10 as shown in FIG. 1. A double shuttle 16 is then shifted from a first position as seen in FIG. 1 to a second position which causes the syringe 15 to be pushed to an aperture 40a (shown in FIG. 2B) in the top of the disposable receptacle 12. The syringe then falls through the aperture 40a, down a chute which will be described in detail later, and finally rests within the receptacle 12. The chute design is shown in FIGS. 7A-7G. Shifting or sliding the shuttle from the first position as seen in FIG. 1 to a second position exposes or opens a second like slot at the other side in the top of the collector 10.

The double shuttle 16 remains in its second position until another syringe is ready for disposal. At that time, the syringe is placed in the now open second slot (36b) in the top of the collector 10. The double shuttle 16 is then moved back into its first position which causes the second syringe to be pushed to a second aperture 40b (FIG. 2B) in the top of the disposable receptacle 12. This second syringe then falls through the second aperture 40b, down a second chute, and finally rests within the disposable receptacle 12. This action also causes the first slot 36a to be again exposed in the top of the collector to receive the next syringe.

The design of the double shuttle 16 permits the sharps collector 10 to remain in a ready-to-use state because either slot 36a or slot 36b can always be exposed and ready to use. In addition, the design of the double shuttle 16 encourages the user to alternate between the two slots 36a and 36b for each use. By alternating between the slots 36a and 36b used, and therefore, the apertures 40a and 40b and associated chutes used, the syringes become distributed in the disposable receptacle 12 more evenly.

Once the disposable receptacle 12 is full, it can be detached from the reusable cover 14 by pushing down on release tabs 32 (shown in FIGS. 1 and 2B). Then aperture covers 68a and 68b (shown in FIGS. 2B and 6) may be snapped closed over the respective apertures 40a and 40b thereby making the receptacle 12 tamper resistant. The receptacle 12 may then be discarded and the cover 14 may be reused to cover another receptacle 12.

Each of the components of the collector will now be described in detail starting with the decorative cover and its associated double shuttle and its guides, and cover release mechanism.

FIGS. 3A-3C show the reusable cover 14 in detail. As shown in FIGS. 3A-3C, the reusable cover 14 includes two end walls 20a and 20b, two side walls 22a and 22b, and a top wall 24. The end walls 20a and 20b, and the side walls 22a and 22b all taper inwardly toward the top wall 24 (note FIGS. 3B and 3C) so covers can be stacked and nested for ease of shipment and storage.

As shown in FIG. 3A, the top wall 24 includes an aperture 26 for the movement of the double shuttle 16, the dimensions of which are important and which will be described in detail later. The inside of top wall 24 also includes eight depending posts 28 for the permanent attachment of guides (which will be described in detail later), and two slots 30 for release tabs 32 (which will be described in detail later) which are used to enable the cover 14 to be readily detached from the disposable receptacle 12. The double shuttle design is shown in FIGS. 4A-4F. The guide design, including the release tabs, is shown in FIGS. 5A-5H.

As shown in FIGS. 4A, 4C, and 4F, the double shuttle 16 includes a centrally disposed handle 34 to facilitate moving it back and forth in the aperture 26 in the cover 14. The double shuttle also includes two slots 36a and 36b (shown in FIGS. 4A and 4F) for receiving used syringes, and inner walls 38a and 38b (shown in FIGS. 4A, 4D, and 4F) which define the slots 36a and 36b and serve to push the used syringes to the respective apertures 40a and 40b (shown in FIGS. 2B and 6A) of the disposable receptacle 12. As shown in FIGS. 4A-4E, the double shuttle 16 also includes two elongated flanges 42. The flanges 42 enable the double shuttle 16 to be held onto the reusable cover 14 via the guides 18 (described in detail below) while still allowing the shuttle 16 to move along the guides via the flanges 42.

FIGS. 5A-5H show one of a pair of guides 18. Two guides 18 are used, one to engage each side of the double shuttle 16 and to attach the double shuttle 16 to the reusable cover 14. The guides 18 engage the flanges 42 of the double shuttle 16 to allow the shuttle 16 to move back and forth with respect to the aperture 26 in the top wall 24 of the receptacle 14. The guides 18 are preferably made from injection molded Delrin plastic.

As shown in FIGS. 5A-5C, each guide 18 includes a release tab 32 which fits into slots 30 (shown in FIGS. 3A and 3B) on the reusable cover 14. The tabs 32 are used to enable the cover 14 to be detached from the disposable receptacle 12. As shown in FIGS. 5A and 5D, each guide 18 also includes holes 44 which fit onto the posts 28 (shown in FIG. 3A) for permanently attaching the guides 18 to the reusable cover 14. Additionally, as shown in FIGS. 5A, 5B, and 5D-5F, each guide 18 has a ledge 46 which fits over a corresponding flange 42 (shown in FIGS. 4A-4E) on the double shuttle 16. Ledge 46 and flange 42 fit in such a way that the double shuttle 16 is permanently attached to the cover 14, yet the flanges 42 of the double shuttle 16 are allowed to freely slide along the ledges 46 of the guides 18, limited in the mount by the walls 38a and 38b of the upstanding handle 34 engaging the edges 26a and 26b of the aperture 26 in the top 24 of the section 14. See FIG. 3A.

As noted earlier the dimensions of the aperture or opening 26 in the top 24 of the top section 14 of the disposable receptacle 12, along with certain dimensions of the double shuttle 16, are important in the design of the present sharps collector 10. The length "L" (note FIG. 4D), of slots 36a and 36b of the double shuttle 16 is determined by the largest syringe size to be used. The width W2 and W3 (note FIG. 4A) of these slots 36a and 36b is the same and is a function on the width of the largest syringe. Thus, the length L and width W2, W3 are a function of the "footprint" of the largest syringe to be deposited in the collector. The amount of travel of the shuttle 16 back and forth within the slot 26, as will be apparent, is a function of the width W1 of slot 26 (FIG. 3A). The widths W2 and W3 of the respective slots 36a and 36b, along with the amount of travel of the shuttle determine the spacings of the apertures 40a, 40b and associated chutes 54 (shown below). The width W4 of the handle 34 is approximately the same as W2, W3.

The drawings in the present application are substantially to scale. In an exemplary embodiment for use with insulin syringes of 0.3, 0.5 and 1.0 ml., the foregoing dimensions are, the length L of slots 36 equals 4.8 inches, the width W1 of the slot 26 equals 1.8 inches, the width W2, W3 of the slots 38a, 38b of the double shuttle 16 are each 0.83 inch the width W4 of the handle 34 is 0.95 inch. The depth of the slots 36a and 36b is whatever depth is required to allow the syringe 15 to lie within the slot and slide under the cover 14 to an aperture 40, and in an exemplary embodiment is 0.40 inch. If the slots 36a and 36b are too wide, then the edge of an aperture 40 and chute 54 will be exposed through opening 26, and if the slots 36a, 36b are too narrow, the syringe will tend to bind within the slot 36.

As shown in FIGS. 5B, 5C, and 5E-5H, each guide 18 also includes downward extending hooks 48 which form part of the locking and release arrangement between the cover and receptacle. The hooks 48 fit into attachment slots 50 (described later) of the disposable receptacle 12 and hold and essentially lock the cover 14 onto the receptacle 12. The hooks 48 can be disengaged from the attachment slots 50 by pressing down on the release tabs 32. Thus, the cover 14 can be released from the receptacle 12 by pressing down on the tabs 32 which cause the lower ends of the tabs 32 to push down on the top surface of the receptacle 12 and, therefore, cause the hooks 48 to pull away and release from the attachment slots 50. The attachment slots 50 of the receptacle 12 are shown in FIG. 6A.

FIGS. 6A-6L, 7A-7G, and 8A-8E show the components of the disposable receptacle 12. As discussed earlier, the receptacle 12 is the container which holds the syringes to be discarded and is disposed of along with any syringes it contains. The receptacle 12 is preferably made from injection molded polypropylene. The receptacle 12 includes a top section 52 (shown in FIGS. 6A-6L), a pair of like chutes 54 (one of which is shown in FIGS. 7A-7G), and a bottom closure 56 (shown in FIGS. 8A-8E). The receptacle 12 is assembled by snapping the chutes into the top section and the top section onto the bottom closure.

FIGS. 6A–6L show a top section 52 of the disposable receptacle 12. As shown in FIGS. 6A–6E the top section 52 of the receptacle 12 includes two end walls 58, a front wall 60, a back wall 62, and a top wall 64. The end walls 58, the front wall 60, and the back wall 62 all taper inwardly toward the top wall 64 to enable the receptacle 12 to be stacked and nested with like receptacles 12 compactly for ease of shipment and storage.

Figure 6J:
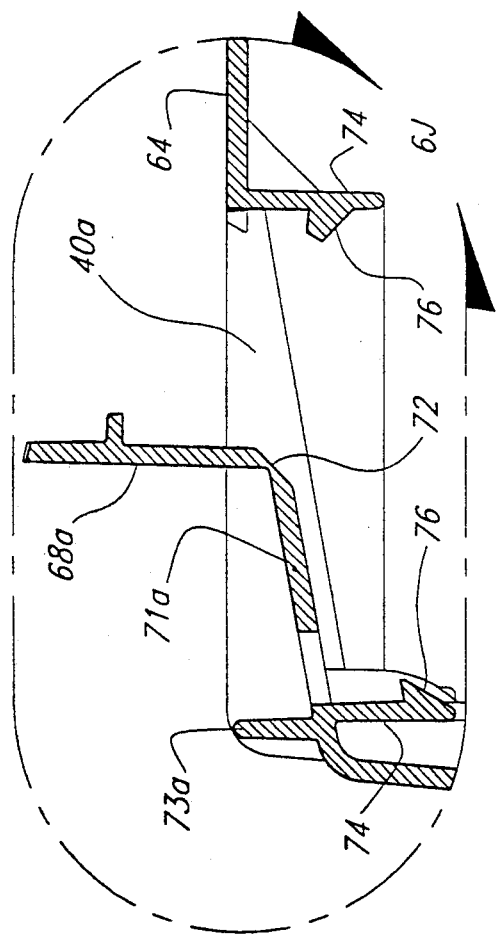
FIG. 6J is an enlarged view of an aperture cover in an open position taken from ellipse 6J in FIG. 6I.
Figure 6L:
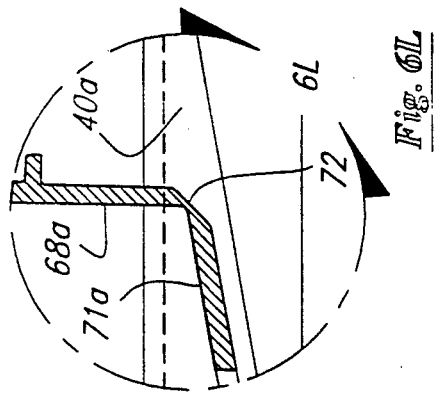
FIG. 6L is a detailed enlargement of a living hinge of an aperture cover taken from circle 6L in FIG. 6I.
Figure 6K:
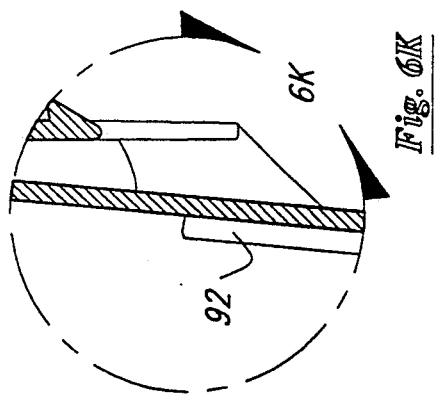
FIG. 6K is an enlarged view of a rib used to hold a handle of the disposable receptacle taken from circle 6K in FIG. 6I.
Figure 9:
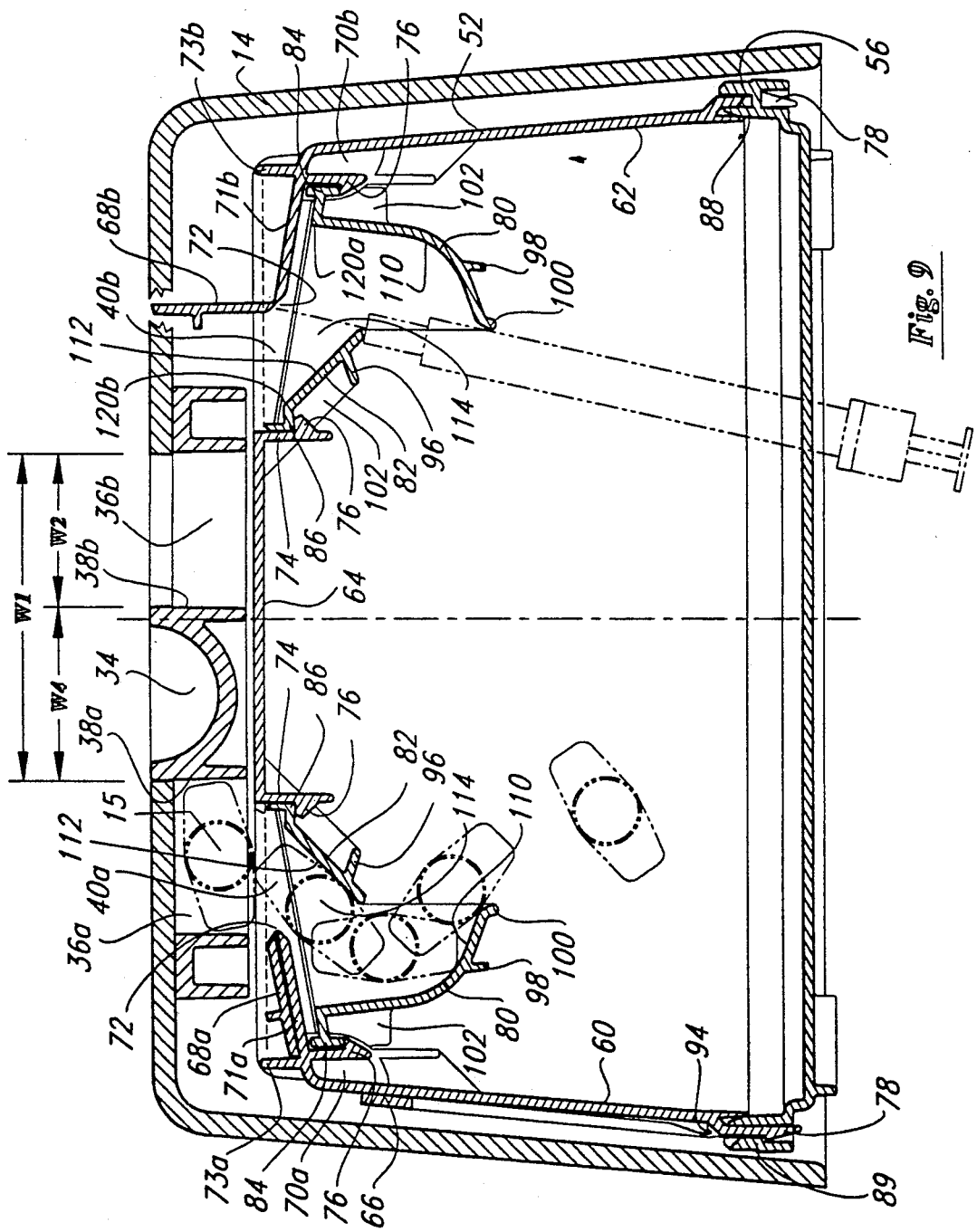
FIG. 9 is a cross-sectional view of the assembled sharps collector illustrating how syringes fall through a chute and cannot readily come back out of a chute.

The top wall 64 of the top section 52 as seen in FIG. 6A includes two apertures 40a and 40b for receiving syringes into the disposable receptacle 12. Two aperture covers 68a and 68b are used to seal off the apertures 40a and 40b when the disposable receptacle is filled and ready for disposal, and two finger indents 70a and 70b are provided to permit the aperture covers 68a and 68b to be easily flipped from their open position to their closed and locked position. Finger indent 70a also permits the handle 66 to be flipped open. As shown in FIGS. 6E, 6I, 6J, and 6L, each aperture cover 68 is attached to the disposable receptacle 12 by a living hinge 72. The living hinges 72 make it possible to easily pivot the aperture covers 68a and 68b from their open positions. The covers 68a and 68b are normally held in their open positions as seen in FIG. 2B because of the relationship of the covers 68, angled walls 71 (note FIGS. 6I and 6J) and ridges 73. When the aperture cover 68a is rotated fully counterclockwise as seen in FIG. 6I and 6J it is held in the fully open position substantially against the wall 71a by the outer end of the cover 68a engaging the inner surface of the ridge 73a. Also see FIG. 9.

The top wall 64 of the top section 52 also includes four attachment slots 50 (FIGS. 6A and 6H) used to affix the reusable cover 14 to the disposable receptacle 12. These attachment slots 50 receive the hooks 48 (shown in FIGS. 5B, 5C, and 5E–5H) of the guides 18 which fasten the cover 14 to the receptacle 12.

As shown in FIGS. 6A, 6E, and 6F, a pull-out handle 66 may be attached to the front wall 60 which may be used to carry the receptacle 12 when the reusable cover 14 is removed. Lower ends 66a and 66b of the handle 66 are attached to the wall 60 and have living hinges 94 to allow the handle to pivot outwardly from the wall 60 as best seen in FIGS. 6A and 6E. As shown in FIGS. 6B, 6E, 6I and 6K, the front wall 60 includes a pair of retainer ribs 92. The ribs 92 are provided to hold the pull-out handle 66 against the front wall 60.

The underside of the top wall 64 of the top section 52 includes several ridges 74 as shown in FIGS. 6B–6F, and 6H–6J which create dams and help prevent liquid substances from leaking out of the receptacle 12 should the sharps collector 10 fall over or be turned over. The ridges 74 also include hooks 76 around the apertures 40 to attach the two chutes (one of which is shown in FIGS. 7A–7G) to the disposable receptacle 12 under the apertures 40.

As shown in FIGS. 6B–6E, and 6G, the bottom edge of the top section 52 includes four offset tabs 78, two extending from each wall 60 and 62, which allow the top section 52 to be snapped onto the bottom closure which will be described in detail below. The offset spacing of the tabs 78 is provided to prevent inadvertent assembly upside down of the top section 52 and the bottom closure. The bottom closure is shown in FIGS. 8A–8E and discussed in more detail later.

FIGS. 7A–7G show details of each of the pair of chutes 54. One chute 54 is disposed in each of the apertures 40a and 40b in the top of the disposable receptacle 12. Each chute 54 is positioned to receive syringes and allow them to fall into the receptacle 12. The chutes 54 are preferably made from injection molded styrene and are designed to obstruct syringes which are contained in the receptacle 12 from protruding or re-emerging from the receptacle 12. See also FIG. 9.

Figure 7A:
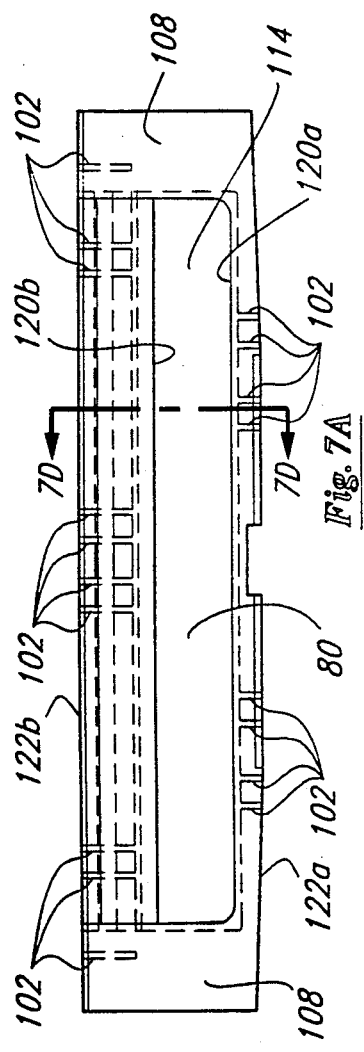
FIG. 7A is a top or plan view of one of a pair of chutes used on the receptacle of the present invention.
Figure 7B:
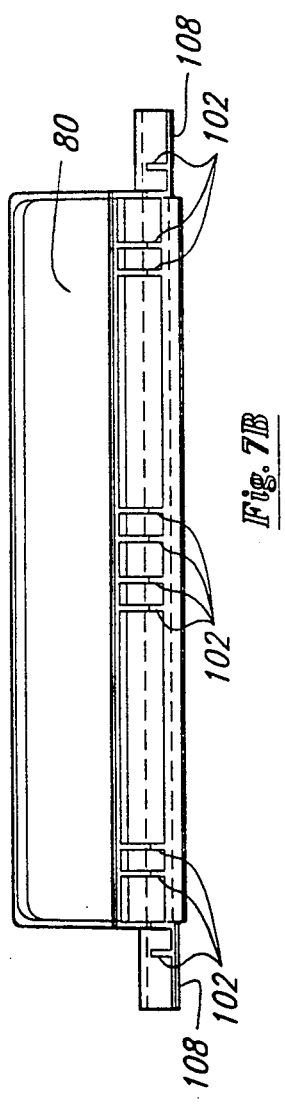
FIG. 7B is a first or front side view of the chute.
Figure 7C:
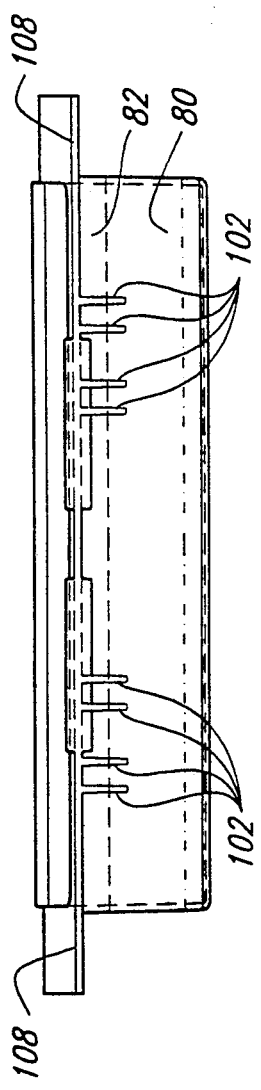
FIG. 7C is a second or back side view of the chute.

Each chute 54 as shown in FIG. 7A includes a top outer flange 108 which frames an opening 114, and has inner edges 120a and 120b and outer edges 122a and 122b. As best seen in FIG. 7D, the opening 114 is defined by a depending arcuate wall 80 and a flat angled wall 82 which extend downward from the inner edges 120a and 120b respectively. The walls 80 and 82 have inner surfaces 110 and 112, respectively, which further define the opening 114 through which a deposited syringe must fall to enter the disposable receptacle 12.

Figures 7H, 7I:
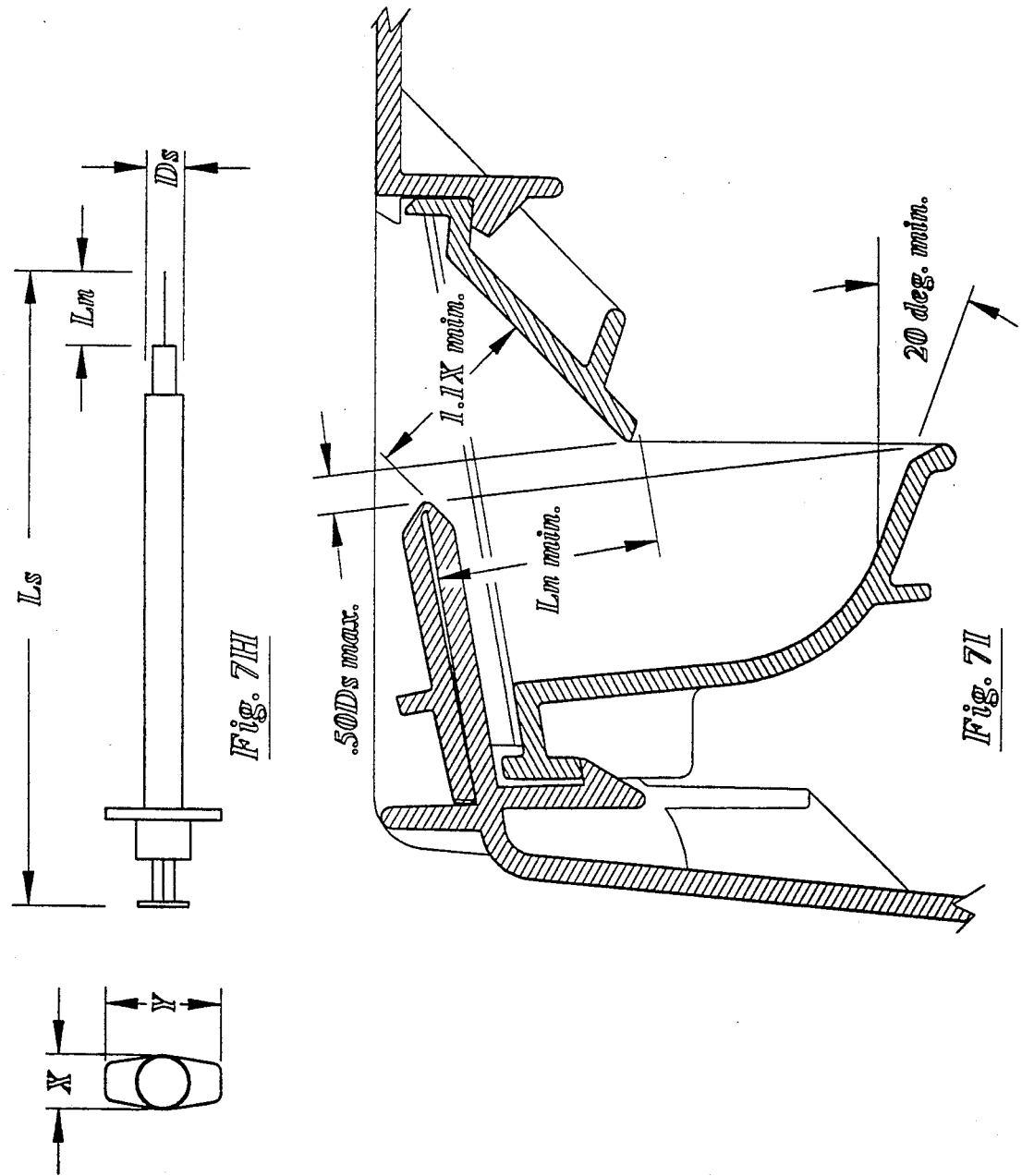
FIG. 7H is a side view and an end view of a sharp in the form of a hypodermic needle.
FIG. 7I is a cross-sectional view of a chute.

The design of the chute opening (which includes parts of the "inner box" and the "chute") for a particular syringe with dimensions and shape similar to FIG. 7H is dictated by the following rules.

1. The width of the line-of-sight gap (FIG. 7I) to be less than ½ of the syringe body diameter (i.e., 50 Ds max.).

2. The depth of the line-of-sight gap (FIG. 7I) from where the syringe body hits the chute to the outside surface to be greater the needle length (i.e., Ln min.).

3. The minimum width of the chute (FIG. 7I) at all points to be greater than 1.1 times the maximum width of the syringe (i.e., 1.1×min.).

4. No surface (FIG. 7I) to be less than 20 degrees from the horizontal.

Figure 7J:
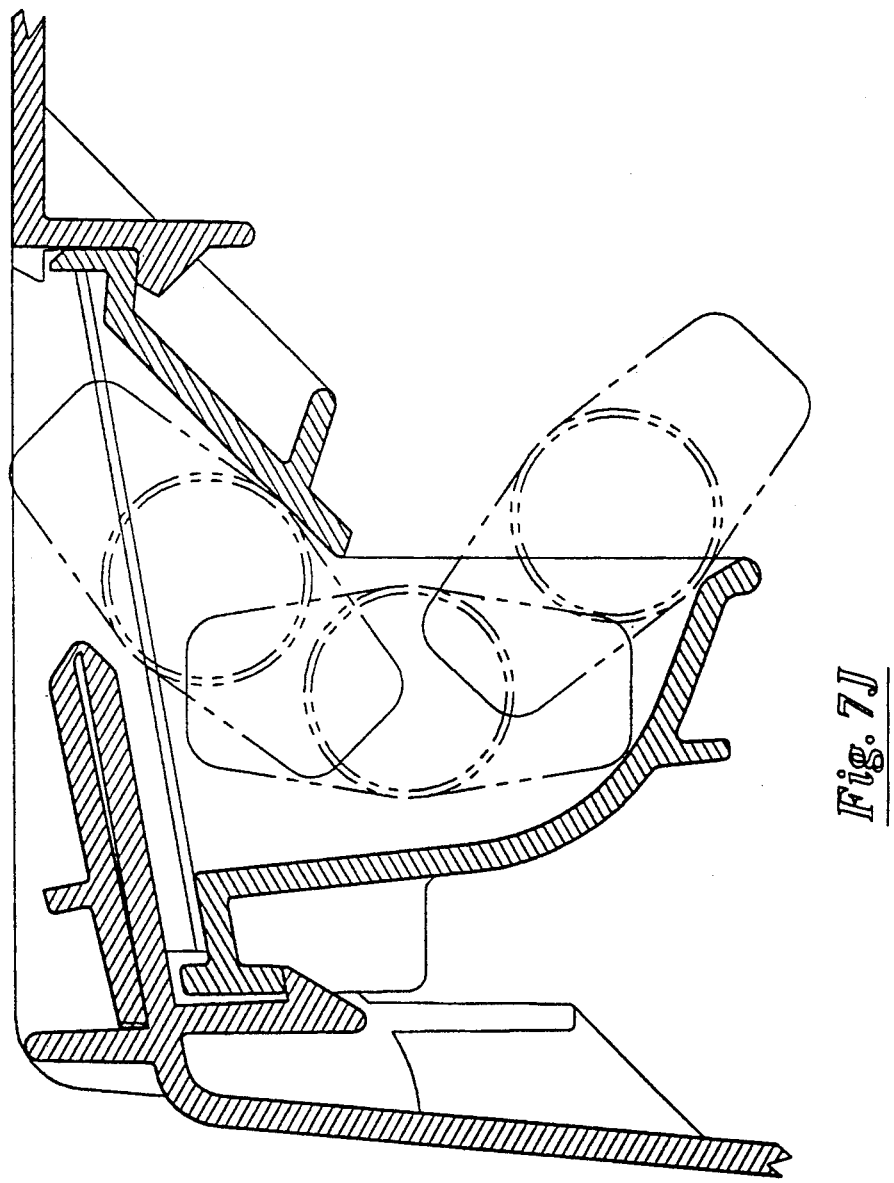
FIG. 7J is a cross-sectional view of a chute showing a path a hypodermic needle takes as it falls through the chute.

5. The minimum envelope of the chute (FIG. 7J) to be a locus of points that allow the maximum syringe profile to pass through without violating rules 1–4.

6. Additional space may be allowed for manufacturing, assembly, etc., that do not violate rules 1–5.

The depending arcuate wall 80 as shown in FIG. 7D extends perpendicular to and downward from the flange 108 at the inner edge 120a and then arcs inwardly towards the flat angled wall 82. The flat angled wall 82 extends downward from the flange 108 at the inner edge 120b and angles inward towards the arcuate wall 80. The walls 80 and 82 are formed integrally with the flange 108. The walls 80 and 82 are designed such that they define the opening 114 so the opening 114 can accommodate several different sizes of syringes as noted earlier, with or without needles, and prevent deposited syringes from exiting the disposable receptacle 12.

As shown in FIGS. 7D–7F the walls 80 and 82 of the chutes 54 also have outer surfaces 116 and 118 respectively. The outer surfaces 116 and 118 include stiffening ribs 96, 98, and 100 which run along the outer surfaces 116 and 118 of the walls 80 and 82 and help maintain the rigidity and straightness of the opening 114 of each chute 54.

The outer edges 122a and 122b as shown in FIGS. 7D and 7G of the flange 108 of each chute 54 include two integrally formed attachment ledges 84 and 86. These ledges 84 and 86 allow the chutes 54 to be snapped onto the hooks 76 on the underside of the top wall 64 of the top section 52 (shown in FIGS. 6B, 6I, and 6J). Thus, by this ledge and hook arrangement each chute 54 is attached to the disposable receptacle 12. Ribs or guards 102 are molded into the chute 54 as seen in FIGS. 7A–7D. These are provided to prevent a needle of a syringe which is in the receptacle from sticking out of the openings or cracks between the edges of the chute 54 and body of the top section 52 of the receptacle 12 where the chute attaches at the aperture 40.

The dimensions, angles, and slopes of each chute 54 are important as an example which is workable for the preferred embodiment. The tolerance of the opening 114 of each chute 54 can be tested by a cylinder and ball test. The opening 114 of each chute 54 should be of a size that allows a cylinder of a particular size to pass through, but does not allow a ball of a particular, slightly larger size to pass through.

FIGS. 8A-8E show a bottom closure 56 for the disposable receptacle 12. As shown in FIGS. 8A-8E, the bottom closure 56 includes a groove 88 all around its outer edge, along with attachment slots 90. The groove 88 is designed such that when the top section 52 and the bottom closure 56 are attached there is a good seal between them which is leak-resistant. The attachment slots 90 are designed to receive the tabs 78 on the bottom edge of the top section 52 (shown in FIGS. 6B-6E, and 6G) and provide a tamper-resistant connection. The slots 90 are spaced such that they will accept the tabs 78 only if the top section 52 and the bottom closure 56 are properly aligned (not upside down). It is preferable that the outer edge 89 adjacent the openings 90 be clear or translucent (or that the closure 56 be clear or translucent), and that the tabs 78 of the top section 52 be of a color (e.g., red) so that the tabs 78 will be visible through the edge 89. This provides a ready indicator to show whether or not the top section 52 and bottom closure 56 are properly attached together.

Although a particular and preferred embodiment of a sharps collector has been shown and described herein for use with several sizes of insulin syringes as discussed earlier, it is to be understood that the collector design can be modified for other sizes and types of syringes, as well as for other sharps type devices. Although a receptacle 12 having a pair of apertures 40 has been shown as a preferred embodiment for distribution of syringes, a single aperture receptacle could be used along with a chute to reduce the chances of syringes reemerging. Even so, some form of shuttle arrangement, although not necessary, still may be desirable for ease of use. Furthermore, the cover 14 and double shuttle arrangement 16 can be used on other forms of receptacles, even conventional forms of receptacles, for facilitating deposit of syringes and other sharps. Also, particularly in the case of a single aperture receptacle, the shuttle can be provided with a spring return.

While an embodiment of the present invention has been shown and described, various modifications may be made without departing from the scope of the present invention, and all such modifications and equivalents are intended to be covered.

What is claimed is:

1. A collector for holding and disposing of syringes comprising a disposable receptacle generally resembling a rectangular box, wherein said receptacle includes an upper receptacle body resembling a box with an open bottom and a lower receptacle closure for connection with said upper receptacle body closing said open bottom of the upper receptacle body to form said disposable receptacle, said disposable receptacle having two substantially parallel elongated apertures, said apertures providing access to a pair of chutes, a pair of chutes mounted onto the disposable receptacle and extending into the receptacle, said chutes being aligned with the elongated apertures of said disposable receptacle, said chutes providing means for guiding and introducing syringes into said disposable receptacle and obstructing contained syringes from protruding or re-emerging from said disposable receptacle, a decorative reusable cover generally resembling a box with an open bottom, said cover being configured to fit over, attach to, and cover said disposable receptacle and be detachable therefrom, said cover being proportioned to conceal the elongated apertures of said receptacle, said cover including an elongated opening for providing access to a double shuttle attached to said cover, and a double shuttle attached to the reusable cover, said double shuttle being movable and providing means by which syringes are discarded into the disposable receptacle through the apertures and chutes of said disposable receptacle when said cover is in place on the receptacle.

2. A collector for holding and disposing of syringes comprising a disposable receptacle generally resembling a rectangular box, wherein said receptacle includes an upper receptacle body resembling a box having a top wall with inner and outer surfaces, four side walls, and an open bottom, and fasteners extending from two of the side walls, and a lower receptacle closure for connection with the four side walls and the fasteners of said upper receptacle body for holding said lower receptacle closure onto said upper receptacle body and closing said open bottom of the upper receptacle body to form said disposable receptacle, said top wall of said disposable receptacle having two parallel elongated apertures, said apertures providing access to a pair of chutes, a pair of chutes mounted onto the top wall of the disposable receptacle and extending into the receptacle, said chutes being aligned with the apertures of said disposable receptacle, said chutes providing means for guiding and introducing syringes into said disposable receptacle and obstructing contained syringes from protruding or re-emerging from said disposable receptacle, a decorative reusable cover generally resembling a box having a top wall with inner and outer surfaces, four side walls, and an open bottom, said cover being configured to fit over, attach to, and cover said disposable receptacle and be detachable therefrom, said cover being proportioned to conceal the elongated apertures of said receptacle, said top wall of said cover including an elongated opening for providing access to a double shuttle attached to said cover, and a double shuttle attached to the top wall of said reusable cover, said double shuttle providing means by which syringes ar discarded into the disposable receptacle through the apertures and chutes of said disposable receptacle when said cover is in place on the receptacle.

3. A collector for holding and disposing of syringes comprising a disposable receptacle generally resembling a rectangular box, wherein said receptacle includes an upper receptacle body resembling a box having a top wall with inner and outer surfaces, four side walls, and an open bottom, and fasteners formed thereon, and a lower receptacle closure with a groove and fasteners formed thereon which correspond to and connect with the four side walls and the fasteners of said upper receptacle body for thereby holding said lower receptacle closure onto said upper receptacle body and closing said open bottom of the upper receptacle body to form said disposable receptacle, said top wall of said disposable receptacle having at least one elongated aperture, each aperture providing access to a chute, a chute mounted onto the inner surface of the top wall of the disposable receptacle, said chute being aligned with the aperture of said disposable receptacle, said chute providing means for guiding and introducing syringes into said disposable receptacle and obstructing contained syringes from protruding or re-emerging from said disposable receptacle, a reusable cover generally resembling a box having a top wall with inner and outer surfaces, four side walls, and an open bottom, said cover being designed to fit over, attach to, detach from, and cover said disposable receptacle, said cover being proportioned to conceal the elongated aperture of said receptacle, said top wall of said cover including an elongated opening for providing access to a shuttle attached to said cover, and a shuttle attached to said reusable cover, said shuttle being movable and providing means by which syringes are discarded into the disposable receptacle through the aperture and chute of said disposable receptacle when said cover is in place on the receptacle.

4. A container for holding and disposing of syringes comprising a disposable receptacle generally resembling a rectangular box, said receptacle including an upper receptacle body resembling a box having a top wall with inner and outer surfaces, four side walls, and an open bottom, and fasteners formed thereon, and a lower receptacle closure with a groove and fasteners formed thereon which correspond to and connect with the four side walls and the fasteners of said upper receptacle body thereby holding said lower receptacle closure onto said upper receptacle body and closing said open bottom of the upper receptacle body to form said disposable receptacle, said top wall of said disposable receptacle having two parallel elongated apertures, said apertures providing access to a pair of chutes, said top wall of said disposable receptacle having attachment slots, said slots providing a means for a cover to attach to and detach from said disposable receptacle, a pair of chutes mounted onto the inner surface of the top wall of the disposable receptacle, said chutes being aligned with the apertures of said disposable receptacle, said chutes providing means for guiding and introducing syringes into said disposable receptacle and obstructing contained syringes from protruding or re-emerging from said disposable receptacle, a reusable cover generally resembling a box having a top wall with inner and outer surfaces, four side walls, and an open bottom, said cover being designed to fit over, attach to, and cover said disposable receptacle and be detachable therefrom, said cove being proportioned to conceal the parallel elongated apertures of said receptacle, said top wall of said cover including an elongated opening for providing access to a double shuttle attached to said cover, said cover having attachment posts on the inner surface of the top wall, said posts providing a means for attaching attachment guides to the reusable cover, said cover having openings providing a means for release tabs to protrude through the cover, a pair of attachment guides having holes which fit onto posts located on the inner surface of the top wall of the reusable cover and attach the guides to the reusable cover, downward extending hooks for attaching the reusable cover to the disposable receptacle by engaging attachment slots formed in the disposable receptacle, upward extending release tabs which fit through openings formed in the reusable cover and, when pressed down, cause the reusable cover to be released from the disposable receptacle by disengaging said attachment hooks from said attachment slots, and attachment ledges for attaching the double shuttle to the reusable cover while allowing manipulation of said double shuttle, and a movable double shuttle attached to the inner surface of the top wall of said reusable cover, said double shuttle providing means by which syringes are discarded into the disposable receptacle through the apertures and chutes of said disposable receptacle when said cover is in place on the receptacle.

5. A disposable receptacle for holding and disposing of syringes comprising an upper receptacle body generally resembling an elongated box comprising four side walls having inner and outer surfaces and a top wall having inner and outer surfaces, said top wall having two substantially parallel elongated apertures therein, said apertures providing access to a pair of chutes mounted to the inner surface of said top wall, said apertures and chutes being adapted to pass syringes, and a lower closure adapted to engage the walls of said receptacle body and attach thereto and form a leak resistant seal between the walls of said receptacle body and said closure.

6. The receptacle according to claim 5 wherein each of the chutes of said upper receptacle body is configured to form an opening defined by a flange which frames the opening and has inner edges which define the opening, and which has outer edges, a depending arcuate wall which initially extends perpendicular to and downward from the flange at the inner edge of the flange, and then arcs inward towards a flat angled wall, and a flat angled wall which extends downward from the flange at the inner edge of the flange and angles inward towards the arcuate wall, and said chutes are mounted directly below and in alignment with the apertures of the top wall of the upper receptacle body, said chutes providing a means through which syringes fall as syringes are dropped through the apertures and become enclosed in and obstructed from protruding or re-emerging from said disposable receptacle.

7. The receptacle according to claim 6 wherein the depending arcuate wall and the flat angled wall of each chute have inner and outer surfaces and ribs are formed integrally with said outer surfaces, said ribs extending along the outer surfaces to increase the rigidity thereof for maintaining the straightness of said opening in the chute.

8. The receptacle according to claim 6 wherein the outer edges of the flange of each chute includes integrally formed attachment ledges, said ledges providing a means for attaching the chutes to the upper receptacle body of the disposable receptacle.

9. The receptacle according to claim 5 wherein the side walls of said upper receptacle body are tapered inward towards the top so that a number of said receptacle bodies may be stacked one inside another for storage.

10. The receptacle according to claim 5 wherein ridges are formed integrally with the inner surface of the top wall of said upper receptacle body, said ridges form dams surrounding the apertures of said upper receptacle body and help prevent leaks of substances from inside the receptacle body through said apertures.

11. The receptacle according to claim 10 wherein said ridges include hooks which allow for the attachment of the chutes onto the inner surface of the top wall of the upper receptacle body.

12. The receptacle according to claim wherein aperture covers are integrally formed with the outer surface of the top wall of the upper receptacle body, said aperture covers normally being retained open to expose said apertures but which for disposal of the receptacle fit over and cover the apertures of said upper receptacle body and help prevent syringes in the receptacle from reemerging.

13. The receptacle according to claim 12 wherein each of said covers is connected to the upper receptacle body by a living hinge.

14. The receptacle according to claim 5 wherein the four side walls of said upper receptacle body comprise two side walls, a back wall, and a front wall, with a pull-out handle integrally formed on the outer surface of said front wall, said handle providing a means for carrying said disposable receptacle.

15. The receptacle according to claim 14 wherein said handle is connected to the front wall of the upper receptacle body by a living hinge.

16. The receptacle according to claim 5 wherein said receptacle is made of injection molded polypropylene.

17. The receptacle according to claim 5 wherein the top wall of the upper receptacle body has attachment slots, said slots providing a means for a cover to attach to and detach from said disposable receptacle, and further comprising a reusable decorative cover which may be attached to and detached from said disposable receptacle, and a pair of attachment guides attached to the reusable cover and have downward extending hooks for attaching the guides and, thus, the reusable cover to the disposable receptacle by engaging attachment slots formed in the disposable receptacle.

18. The receptacle according to claim 5 further comprising a reusable decorative cover which may be attached to and detached from said disposable receptacle, said reusable cover generally resembling an elongated box comprising four side walls and a top wall having inner and outer surfaces, said top wall having an elongated opening located therein, said opening permitting manipulation of a double shuttle, and a generally rectangular double shuttle movably attached to the inner surface of the top wall of said reusable cover, and said double shuttle having walls defining parallel elongated slots for receiving syringes, said walls providing a means for pushing syringes toward the apertures of said disposable receptacle.

19. The receptacle according to claim 18 wherein the reusable cover has a pair of attachment guides having holes which fit onto posts located on the inner surface of the top wall of the reusable cover and attach the guides to the reusable cover, downward extending hooks for attaching the guides and, thus, the reusable cover to the disposable receptacle by engaging attachment slots formed in the disposable receptacle, upward extending release tabs which fit through slots formed in the reusable cover and, when pressed down, cause the reusable cover to be released from the disposable receptacle by disengaging said attachment hooks from said attachment slots, and attachment ledges for attaching the double shuttle to the reusable cover while allowing sliding movement of said double shuttle.

20. The receptacle according to claim 19 wherein the inner surface of the top wall of said cover has attachment posts, said posts providing a means for attaching the attachment guides to the reusable cover.

21. The receptacle according to claim 18 wherein the double shuttle has a handle member between the parallel slots, said handle member extending slightly taller than the remainder of said double shuttle and protruding out of, but narrower than, the elongated opening in the reusable cover, said handle providing a means for moving said double shuttle back and forth in said opening and limiting such movement to the width of said elongated opening of the reusable cover.

22. The receptacle according to claim 18 wherein the double shuttle has two attachment flanges, said flanges providing a means for movably attaching said double shuttle to the reusable cover.

23. The receptacle according to claim 5 wherein one of either the upper receptacle body or the lower closure has a plurality of colored locking tabs and the other is formed to allow the tabs to be viewed to visibly indicate to the user whether or not the upper receptacle body and the lower closure are locked together.

24. The receptacle according to claim 5 wherein the upper receptacle body has a plurality of colored locking tabs and the lower closure is formed to allow the tabs to be viewed to visibly indicate to the user whether or not the upper receptacle body and the lower closure are locked together.

25. A disposable receptacle for holding and disposing of syringes comprising an upper receptacle body generally resembling an elongated box having two parallel elongated apertures therein, said apertures providing access to a pair of chutes connected with the receptacle body, said apertures and chutes being adapted to pass syringes, a lower closure adapted to engage the walls of said receptacle body and attach thereto and form a leak resistant seal between the walls of said receptacle body and said closure, and each chute comprising defining an opening having inner and outer edges, a dependent arcuate wall which initially extends perpendicular to and downward from the chute at the inner edge of the opening, and then arcs inward towards a flat angled wall, and a flat angled wall which extends downward from the chute at the inner edge of the opening and angles inward towards the arcuate wall, and said chutes providing a means through which syringes fall as syringes are dropped through the apertures of the upper receptacle body and obstructing syringes from protruding or re-emerging from said disposable receptacle.

26. A reusable cover generally resembling a rectangular box comprising four side walls and a top wall having inner and outer surfaces, said top wall having an elongated opening located therein, said opening permitting manipulation of a double shuttle, and a generally rectangular double shuttle movably attached to the inner surface of the top wall of said reusable cover, said double shuttle having walls defining parallel elongated slots for receiving syringes, said walls providing a means for pushing syringes toward the apertures of a disposable receptacle.

27. A reusable cover generally resembling a rectangular box and having an elongated opening located therein, said opening permitting access to a double shuttle, and a generally rectangular double shuttle movably attached to the reusable cover, said double shuttle having walls defining parallel elongated slots for receiving syringes, said walls providing a means for pushing syringes toward apertures of a disposable receptacle enclosed by said reusable cover, said double shuttle also having a handle member between the parallel slots, said handle member extending slightly taller than the remainder of said double shuttle and protruding out of, but narrower than, the elongated opening in the reusable cover, said handle providing a means for moving said double shuttle back and forth in said opening and limiting such movement to the width of said elongated opening of the reusable cover.

28. An apparatus for receiving and storing for disposal syringes and the like comprising a disposable receptacle body substantially in the form of a rectangular box having a top with a plurality of substantially parallel and elongated apertures for receiving syringes therethrough for distribution within the receptacle body, the receptacle having a removable bottom closure which can be substantially locked and sealed with the bottom of the receptacle body, a shuttle assembly having at least one elongated opening for initially receiving each syringe and being movable with respect to the top of the receptacle body for pushing a syringe substantially horizontally into respective aperture of the receptacle body, and chutes disposed with respect to the apertures in the receptacle body for allowing syringes to fall through an aperture into the receptacle body, and the chutes being configured to substantially prevent reemergence of a syringe from the receptacle body.

29. An apparatus as in claim 28 including a decorative cover adapted to fit over and cover the receptacle, the cover having an elongated opening through which syringes can pass to the shuttle, the shuttle underlying the cover and being adapted to move back and forth with respect to said opening to allow syringes to be distributed first to one elongated aperture and then to the other.

30. An apparatus as in claim 28 wherein the elongated apertures in the receptacle and the elongated opening in the shuttle being configured for receiving syringes therein in a horizontal orientation to allow syringes to be deposited in the shuttle horizontally and to drop horizontally through the apertures into the receptacle.

* * * * *

UNITED STATES PATENT AND TRADEMARK OFFICE
CERTIFICATE OF CORRECTION

PATENT NO. : 5,184,720

DATED : February 9, 1993

INVENTOR(S) : Packer, et al.

It is certified that error appears in the above-identified patent and that said Letters Patent is hereby corrected as shown below:

Column 13, line 24, after "claim" add ---5---.

Signed and Sealed this

Twenty-first Day of June, 1994

Attest:

BRUCE LEHMAN

*Attesting Officer*  *Commissioner of Patents and Trademarks*